United States Patent [19]

Stiffey

[11] Patent Number: 5,192,667
[45] Date of Patent: Mar. 9, 1993

[54] METHOD FOR EVALUATING ANTI-FOULING PAINTS

[75] Inventor: Arthur V. Stiffey, Slidell, La.

[73] Assignee: The United States of America as represented by the Secretary of the Navy, Washington, D.C.

[21] Appl. No.: 394,400

[22] Filed: Aug. 15, 1989

[51] Int. Cl.$^5$ .............................................. C12Q 1/18
[52] U.S. Cl. ........................................ 435/32; 435/29; 435/258; 435/947; 106/15.05
[58] Field of Search .................. 435/29, 32, 258, 947; 106/15.05

[56] References Cited

U.S. PATENT DOCUMENTS 4,950,594  8/1990  Stiffey .................................... 435/32

Primary Examiner—Ameila Burgess Varbrough
Attorney, Agent, or Firm—Thomas M. Phillips; Thomas E. McDonnell; Barry A. Edelberg

[57] ABSTRACT

A method of evaluating marine paints for their ability to inhibit growth and attachment of organisms to ship bottoms, to find chemicals toxic to marine fouling organisms and to permit rapid formulation of superior anti-fouling paints, using a bioluminescent microbiological assay. The bottoms of test vials are coated with a paint solution, the paint dried, and identical aliquots of an assay medium containing *Pyrocystis lunula* cells are added to the tests vials and to identical (but unpainted) control vials. After a preselected settling time, the vials are agitated and their light outputs measured and compared. Any dimuition of light in the test vials, relative to the control vials, in an indication of the anti-fouling characteristics of the paints being tested.

14 Claims, No Drawings

METHOD FOR EVALUATING ANTI-FOULING PAINTS

CROSS-REFERENCE TO RELATED APPLICATIONS

Cross-reference is made to the U.S. patent application of the applicant, Arthur V. Stiffey, Ser. No. 07/135,969, filed Dec. 12, 1987, entitled MICROBIOLOGICAL ASSAY USING BIOLUMINESCENCE ORGANISM, now U.S. Pat. No. 4,950,594, which describes the bioluminescent microbiological assay used in the invention described herein.

Cross-reverence is also made to U.S. patent application Ser. No. 07/534,082 of the applicant, entitled STRESS.

BACKGROUND OF THE INVENTION

The invention relates to a method for testing marine paints for anti-fouling ability, i. e., the ability to inhibit growth and attachment of fouling organisms.

In the past, the anti-fouling abilities of marine paints have been evaluated by painting steel plates with the marine paints to be evaluated, immersing the plates in a sea water medium containing fouling organisms, such as barnacles and algae, and observing the attachment of the fouling organisms to the painted plates. Such test procedures are time consuming and expensive, requiring a considerable number of personnel to evaluate and to grow and maintain the test organisms.

SUMMARY OF THE INVENTION

It is a primary object of the invention to provide a rapid and inexpensive method of evaluating the anti-fouling characteristics of marine paints.

In the method of assaying marine paints, according to the invention, a preselected volume of a marine paint solution is introduced into a test container to cover the container bottom. The container is heated for a sufficient time for the paint solution to dry and form a dried coating of paint on the container bottom. A preselected volume of assay medium containing a known quantity of bioluminescent dinoflagellate cells is added to the test container, and the dinoflagellate cells are allowed to settle to the painted bottom of the container. After a preselected settling time, the assay medium in the test container is vigorously agitated to subject the dinoflagellate cells to a shear stress causing them to emit light. The assay medium is agitated for a sufficient time to exhaust the light generating ability of the dinoflagellate cells, during which time the cumulative light output of the agitated assay medium is measured.

The same test procedure can be performed using an identical test container, except no paint solution is introduced into the container, to obtain a control or reference light output measurement for comparison with the light output measurement of the assay medium in the test container holding the paint sample. If the paint sample does not have any ability to inhibit the attachment and growth of marine fouling organisms, the light output of the assay medium in contact with the paint will be approximately the same as the reference light output. Any diminution of the light output of the assay medium in contact with the paint being tested, relative to the reference light output, is an indication that the paint includes active anti-fouling substances. The greater this dimunition of light, the greater the ability of the paint to inhibit the attachment and growth of marine fouling organisms.

DESCRIPTION OF THE PREFERRED EMBODIMENTS

The invention described herein makes use of the microbiological assay described in the above-referenced U.S. patent application, Ser. No. 07/135,969.

The assay organism, the marine dinoflagellate *Pyrocystis lunula*, contains many cysts which emit light when the organism is subjected to a shear stress, such as in stirring. It has a slow rate of growth (doubling time is approximately four days) and transfers need only be done monthly. These organisms require no special handling and benefit from very static conditions. Stock cultures contain approximately 2000 cells/ml. *Pyrocystis lunula* is maintained in culture on f/2 medium, described by Gaillard and Ryther, "Studies on Marine Planktonic Diatoms", Can. Jour. Microbiol. 8, 229, 1962.

| Composition of f/2 Medium | |
|---|---|
| $NaNO_3$ | 150 mg |
| $NaH_2PO_4.H_2O$ | 10 mg |
| Fe sequestrene* | 10 mg (1.3 mg Fe) |
| $Na_2SiO_3.9H_2O$ | 30–60 mg (3–6 mg Si) |
| Vitamins: | |
| Thiamine.HCl | 0.2 mg |
| Biotin | 0.001 mg |
| $B_{12}$ | 0.001 mg |
| Trace metals: | |
| $CuSO_4.5H_2O$ | 0.0196 mg (0.005 mg Cu) |
| $ZnSO_4.7H_2O$ | 0.044 mg (0.01 mg Zn) |
| $CoCl_2.6H_2O$ | 0.020 mg (0.005 mg Co) |
| $MnCl_2.4H_2O$ | 0.360 mg (0.1 mg Mn) |
| $Na_2MoO_4.2H_2O$ | 0.0126 mg (0.005 mg Mo) |
| Sea water | To 2 liters |

*Sodium iron salt of ethylene dinitrilotetraacetic acid (EDTA).

Ferric chloride and EDTA or the sodium salt of EDTA can be mixed to give the same amounts of iron and the chelator; the pH is adjusted to about 4.5.

This medium was modified by the omission of silicate and the addition of TRIS buffer to increase the final pH to 7.6. Artificial sea water is the base for this medium and is prepared with C.P. salts and distilled water from the formula of Lyman and Fleming, "Composition of Sea Water", J. Mar. Res. 3, 134, 1940, given in the following tabulation for synthetic sea water of chlorinity 19.00%.

| salt | Grams |
|---|---|
| NaCl | 23.477 |
| $MgCl_2$ | 4.981 |
| $Na_2SO_4$ | 3.917 |
| $CaCl_2$ | 1.102 |
| KCl | 0.664 |
| $NaHCO_3$ | .192 |
| KBr | .096 |
| $H_3BO_3$ | .026 |
| $SrCl_2$ | .024 |
| NaF | .003 |
| Sum | 34.382 |
| $H_2O$ to | 1000.000 |

The temperature of incubation is $20° \pm 1°$ C. Illumination is provided by cool white flourescent lamps, shaded to obtain a light intensity of 17 micro einsteins/$cm^2$. Illumination is on a cycle of 12 hours light and 12 hours dark. Cells are counted with the aid of a Sedwick Rafter chamber and their concentration adjusted to 100 cells per ml. for use as the assay medium of the method of assaying marine paints described herein.

Antifouling paints are usually prepared by the addition of toxic substances to a basic paint formulation designed to keep the toxicants suspended and capable of being painted on surfaces. Other chemicals may be added to prevent settling, enhance drying, and produce color of the finished product. These paints are insoluble in sea water and therefore difficult, if not impossible, to assay unless permitted to dry on surfaces.

This problem is solved by diluting a viscous paint to be tested with a suitable paint solvent such as acetone, butanol, or benzine, then layering a preselected quantity of the paint solution onto the bottom of an assay vial, and heating the vial to 150° C. for 30 minutes. This process, in effect, paints the bottom of the vial and drives off volatile substances generally insoluble in a sea water medium. When the assay medium described above is added to the vial, the *Pyrocystis lunula* cells quickly settle to the bottom of the vial and thus come in close contact with the paint layer.

In a typical paint assay experiment, 22.5 grams of naval anti-fouling paint CG47 manufactured by the Mobile Paint Manufacturing Company of Mobile, Ala., were weighed out and suspended in 25 ml of acetone in a volumetric flask. The paint sample was shaken vigorously and serial dilutions prepared in acetone of 900 mg/ml, 90 mg/ml, 9 mg/ml, 0.9 mg/ml, 0.09 mg/ml, and 0.009 mg/ml. One ml of each dilution was placed in each of four glass test vials, 22 mm×50 mm. The test vials were heated to 150° C. for 30 minutes, cooled and 3 ml of the assay medium containing 300 *Pyrocystis lunula* cells total (100 cells/ml) were added to each test vial. Five additional vials were set aside as controls and contained only 3 ml of assay medium each (no paint). All vials were placed in a carousel and kept motionless in the dark for about 4.5 hours prior to the assay.

To be certain that the dinoflagellate culture emits the maximum quantity of light, it is necessary that the culture be stirred vigorously. Stirring was accomplished with an acrylic rod equipped on one end with a thin strip of acrylic plastic. The other end of the rod was fitted into the chuck of a variable speed electric motor drive set at about 100 rpm. During the assay of each test or control vial, the rod was inserted approximately ⅔ of the way into the assay medium of the vial, and stirring was continued for about 2 minutes to make sure that the light producing ability of the dinoflagellate cells was exhausted.

Bioluminescence was measured with a solid state photometer described in U.S. Pat. No. 4,689,305 to Stiffey et al, incorporated herein by reference. A multirange stripchart recorder with a chart speed of 5 cm/minute was connected to the photometer which was adjusted such that the recorder registered the cumulative light fluxes as a function of time.

The percentage of bioluminescent quenching is calculated with the following equation:

$$\% \text{ quenching} = \frac{C - E}{C} \times 100$$

where C=displacement of the recorder pen, in mm, during stirring of the control culture, and E=the displacement of the pen during stirring of the test culture.

The results of this paint assay experiment were as follows:

| Paint weights in Vial | % Quenching |
|---|---|
| 900 mg | 100 |
| 90 mg | 100 |
| 9 mg | 100 |
| .9 mg | 100 |
| .09 mg | 25 |
| .009 mg | 0 |

These results indicate that there is a dose response with bioluminescence in the presence of varying weights of paint layers on the bottom of the painted vials.

The assay method described above can be easily modified to permit swift evaluation of leaching rates so important in developing sustained release formulations by extending and varying the contact times with the assay organism.

For example, identical dilutions of the paint to be tested can placed in a selected number of the glass test vials, and the vials heated to produce respective dry coatings of paint on the vial bottom surfaces, as described above. Identical aliquots of assay medium containing the *Pyrocystis lunula* cells are respectively added to the "painted" test vials and to an equal number of identical but unpainted control vials, and all of the vials are kept motionless until tested. After a first "settling" time, a first test vial and a first control vial are assayed as described above.(Each vial is vigorously agitated for a sufficient time to exhaust the light producing capabilities of the dinoflagellate cells while its total light output is measured, and the two light measurements are compared to determine the degree of light diminution, if any.) Similiarly, after a second settling time, a second test vial and a second control vial are assayed, and so forth, until all corresponding pairs of test and control vials have been assayed after different settling times. The variation of light diminution with time is a measure of the degree of leaching of the anti-fouling substance from the paint being evaluated.

The results of this test may also be a measure, to some extent, of the time the medium organisms are in contact with the anti-fouling substance. Also, this test can only be conducted over a relatively short time period—a few days—because of the care required by the medium organisms. However, it may be useful as an inexpensive and quick way of comparing the anti-fouling characteristics of several marine paints.

In a second method of assaying the leaching rate of the anti-fouling material in a marine paint, identical aliquots of sea water (rather than assay medium) are respectively introduced in the preselected number of identically "painted" test vials and the equal number of unpainted control vials described above. After a preselected first "leaching" time (which may be of any desired length - hours, days or months) a first pair of vials, consisting of one test vial and one control vial, is assayed in one of the two ways described below. Similarly, after a preselected second "leaching" time, a second pair of test and control vials is assayed in the same way, and so forth, until all of the test and control vials have been assayed in the same way.

In the first way of assaying a pair of vials, predetermined equal numbers of *Pyrocystis lunula* cells in suspension are added to the test vial and the control vial, respectively. After a preselected settling time during which the two vials are kept motionless in the dark, the two vials are assayed as described above.(Each vial is vigorously agitated for a sufficient time to exhaust the light producing capabilities of the dinoflagellate cells while its total light output is measured, and the two light measurements are compared to determine the degree of light diminution)

In the second way of assaying a pair of vials, the sea water in the test vial is transferred to an additional, clean, "unpainted" test vial and this additional test vial and the control vial are assayed in an identical manner to that described above in the first way of assaying a pair of vials.

In this second method of assaying the leaching rate of a marine anti-fouling paint, the diminution of light with time provides an indication of the leaching rate of the anti-fouling substance in the paint, regardless of which of the above-described first and second ways of assaying a pair of vials is used.

There is a third way of assaying a pair of vials which may be used with the second method of assaying the leaching rate of an anti-fouling paint. In this third way, the sea water is removed from both the test vial and the control vial, and equal quantities of the assay medium described above are respectively introduced into the test vial and the control vial. These vials are then assayed in the same manner as described above for the first or second way of assaying a pair of vials. However, when this third way is used, the assay results are an indication of the remaining anti-fouling capability of the paint, rather than its leaching rate.

The rapid and inexpensive methods described above, for evaluating the ability of marine paints to inhibit growth and attachment of organisms to ship bottoms, can be utilized to find chemicals toxic to marine fouling organisms and to permit rapid formulation of superior anti-fouling marine paints.

There are many variations, additions and modifications to the preferred embodiments of the invention described herein which would be obvious to one skilled in the art. Therefore, it is intended that the scope of the invention be limited only by the appended claims.

What is claimed and desired to be secured by Letters Patent of the United States is:

1. A method of assaying marine paints for their ability to inhibit attachment and growth of marine fouling organisms, which comprises the steps of:
    applying a preselected volume of a marine paint solution to a bottom surface in a first test container;
    drying the paint solution to form a dried paint coating on the first test container bottom surface;
    adding a preselected volume of an assay medium to the first test container, the assay medium containing a predetermined number per unit volume of bioluminescent dinoflagellate cells of the genus Pyrocystis;
    after a preselected settling time, agitating the dinoflagellate cells in the first test container for a preselected agitation time while simultaneously measuring the light output of the dinoflagellate cells in the first test container.

2. A method of assaying marine paints, as described in claim 1, wherein the dinoflagellate cells are *Pyrocystis lunula* cells.

3. A method of assaying marine paints, as described in claim 1, which further comprises the steps of:
    adding an equal preselected volume of the assay medium to a first control container identical to the first test container;
    after an equal preselected settling time, agitating the dinoflagellate cells in the first control container for an equal preselected agitation time while simultaneously measuring the light output of the dinoflagellate cells in the first control container; and
    comparing the light output of the dinoflagellate cells in the first test container with the light output of the dinoflagellate cells in the first control container to determine any diminution of light output.

4. A method of assaying marine paints, as described in claim 3, which further comprises the steps of:
    after drying the paint solution and at a preselected leaching time before adding the assay medium to the first test container, adding a preselected volume of sea water to the first test container; and
    at the same preselected leaching time before adding the assay medium to the first control container, adding an identical volume of sea water to the first control container.

5. A method of assaying marine paints, as described in claim 3, which, after the step of drying the paint solution and before the step of adding the assay medium to the first test container, further comprises the steps of:
    adding a preselected volume of test sea water to the first test container; and
    after a preselected leaching time, removing the test sea water from the first test container.

6. A method of assaying marine paints, as described in claim 3, wherein the dinoflagellate cells are *Pyrocystis lunula* cells.

7. A method of assaying marine paints for their ability to inhibit attachment and growth of marine fouling organisms, which comprises the steps of:
    applying a preselected volume of a marine paint solution to a bottom surface in a first one of two identical test containers;
    drying the paint solution to form a dried paint coating on the first test container bottom surface;
    respectively adding identical preselected volumes of test sea water to the first test container and a first control container which is identical to the second test container;
    after a preselected leaching time, transferring the volume of test sea water from the first test container to the second test container;
    respectively adding identical preselected volumes of an assay medium to the first control container and the second test container, the assay medium container a predetermined number per unit volume of bioluminescent dinoflagellate cells of the genus Pyrocystis;
    after a preselected settling time, agitating the dinoflagellate cells in the second test container for a preselected agitation time while simultaneously measuring the light output of the dinoflagellate cells in the second test container;
    after an equal preselected settling time, agitating the dinoflagellate cells in the first control container for an equal preselected agitation time while simultaneously measuring the light output of the dinoflagellate cells in the first control container; and
    comparing the light output of the dinoflagellate cells in the second test container with the light output of the dinoflagellate cells in the first control container to determine any diminution of light output.

8. A method of assaying marine paints, as described in claim 7, wherein the dinoflagellate cells are *Pyrocystis lunula* cells.

9. A method of assaying marine paints for their ability to inhibit attachment and growth of marine fouling organisms, which comprises the steps of:
   preparing serial dilutions of a marine paint and a paint solvent to obtain a plurality of equal volume paint solution samples, each sample having a different paint/solvent ratio;
   respectively adding the plurality of paint solution samples to a like plurality of identical test containers to cover corresponding bottom surfaces of the test containers;
   drying the plurality of paint solution samples to form a plurality of equal area dried paint coatings on the like plurality of test container bottom surfaces, respectively, each coating having a different thickness;
   preparing an assay medium containing a predetermined number per unit volume of bioluminescent dinoflagellate cells of the genus Pyrocystis in suspension;
   removing a plurality of identical aliquots from the assay medium, including a plurality of test aliquots corresponding respectively to the plurality of dried paint coatings and a reference or control aliquot;
   respectively adding the plurality of test aliquots to the like plurality of test containers to cover the plurality of dried paint coatings with assay medium;
   adding the control aliquot to a control container which is identical to one of the plurality of test containers;
   after a preselected settling time, respectively agitating the control aliquot and the plurality of test aliquots for a preselected agitation time, and simultaneously measuring the light outputs of the control aliquot and the plurality of test aliquots; and
   comparing the light output of the control aliquot with the respective light outputs of the plurality of test aliquots to determine any diminution of light output which is an indication of the ability of the marine paint to inhibit growth and attachment of fouling organisms.

10. A method of assaying marine paints, as described in claim 9, wherein the dinoflagellate cells are *Pyrocystis lunula* cells.

11. A method of assaying marine paints for their ability to inhibit attachment and growth of marine fouling organisms, which comprises the steps of:
   preparing a plurality of identical samples of marine paint solution;
   respectively adding the plurality of paint solution samples to a like plurality of identical test containers to cover corresponding bottom surfaces of the test containers;
   drying the plurality of paint solution samples to form a plurality of identical dried paint coatings on the like plurality of test container bottom surfaces, respectively;
   preparing an assay medium containing a predetermined number per unit volume of bioluminescent dinoflagellate cells of the genus Pyrocystis in suspension;
   removing identical aliquots from the assay medium, including a plurality of test aliquots corresponding respectively to the plurality of dried paint coatings and a like plurality of reference or control aliquots which are associated respectively with the plurality of test aliquots to form a plurality of aliquot pairs, each aliquot pair consisting of a test aliquot and a control aliquot, and each aliquot pair being associated with a preselected settling time;
   respectively adding the plurality of test aliquots to the like plurality of test containers;
   respectively adding the plurality of control aliquots to a like plurality of control containers which are identical to the test containers;
   after the associated preselected settling time, agitating each aliquot for a preselected agitation time, and simultaneously measuring the light output of the aliquot; and
   comparing the light output of each control aliquot of each aliquot pair with the light output of the test aliquot of the pair, to determine any diminution of light output which is an indication of the ability of the marine paint to inhibit growth and attachment of fouling organisms.

12. A method of assaying marine paints, as described in claim 11, wherein each preselected settling time is different from every other preselected settling time.

13. A method of assaying marine paints, as described in claim 11, wherein each preselected settling time is identical to every other preselected settling time and the method further comprises, after the step of drying the plurality of paint samples and before the step of removing the plurality of aliquots from the assay medium, the additional steps of:
   preparing a plurality of identical sea water samples corresponding respectively to the plurality of test containers and associated respectively with a like plurality of non-identical leaching times;
   respectively adding the plurality of sea water samples to the like plurality of test containers, to cover each dried paint coating with sea water; and
   after the associated leaching time, removing each sea water sample from its corresponding test container.

14. A method of assaying marine paints, as described in claim 11, wherein the dinoflagellate cells are *Pyrocystis lunula* cells.

* * * * *